(12) United States Patent
McCann et al.

(10) Patent No.: US 6,593,573 B1
(45) Date of Patent: Jul. 15, 2003

(54) CHEMICAL SPECIES DISTRIBUTION AND MIXTURE MONITORING

(75) Inventors: Hugh McCann, Stockport (GB); Krikor Bertch Ozanian, Stockport (GB); Stephen John Carey, Sheffield (GB); Francis Peter Hindle, Orange-Over-Sands (GB)

(73) Assignee: The University of Manchester Institute of Science and Technology, Manchester (GB)

( * ) Notice: Subject to any disclaimer, the term of this patent is extended or adjusted under 35 U.S.C. 154(b) by 0 days.

(21) Appl. No.: 09/831,588

(22) PCT Filed: Nov. 11, 1999

(86) PCT No.: PCT/GB99/03714

§ 371 (c)(1),
(2), (4) Date: Jul. 16, 2001

(87) PCT Pub. No.: WO00/28304

PCT Pub. Date: May 18, 2000

(30) Foreign Application Priority Data

Nov. 11, 1998 (GB) ............................................... 9824690
Nov. 11, 1998 (GB) ............................................... 9824693

(51) Int. Cl.⁷ ............................................... G01N 21/63
(52) U.S. Cl. ........................... 250/339.12; 250/339.01; 250/458.1
(58) Field of Search ...................... 250/339.12, 339.01, 250/339.06, 458.1, 459.1, 461.1; 356/61

(56) References Cited

U.S. PATENT DOCUMENTS

| | | | |
|---|---|---|---|
| 5,139,334 A | | 8/1992 | Clarke |
| 5,384,467 A | | 1/1995 | Anton |
| 5,758,653 A | * | 6/1998 | Schotland ............... 128/665 |
| 5,762,607 A | * | 6/1998 | Schotland et al. ........ 600/407 |
| 5,798,840 A | | 8/1998 | Beiting |

FOREIGN PATENT DOCUMENTS

| | | |
|---|---|---|
| DE | 19932202 | 3/2000 |
| WO | WO 96/26431 | 8/1996 |
| WO | WO 98/30889 | 7/1998 |

OTHER PUBLICATIONS

H. Zhao and N. Ladommatos, "*Optical diagnostics for in–Cylinder Mixture Formation Measurements in IC Engines,*" Dept. of Mechanical Engineering, Brunel University, Uxbridge, UK, Prog. Energy Combust. Sci. vol. 24, pp. 297–336, 1998.

D. Desenne et al., "*Pulsed Multichannel Raman Spectroscopic Investigation of the Spatial Distribution of Molecular Species in a Engine,*" Proceedings of the Tenth Int'l Conf. On Raman Spectroscopy, 1986.

Robert Cesareo and Sergio Mascarenhas, "*A New Tomographic Device Based on the Detection of Fluorescent X–Rays,*" Nuclear Instruments & Methods in Physics Research, Amsterdam, 1989.

* cited by examiner

Primary Examiner—Constantine Hannaher
Assistant Examiner—Timothy Moran
(74) Attorney, Agent, or Firm—Woodard, Emhardt, Naughton, Moriarty & McNett LLP

(57) ABSTRACT

An apparatus for monitoring the distribution of a chemical species within a defined space, for example a vessel such as an internal combustion engine cylinder. A plurality of radiation sources and radiation detectors are distributed around the perimeter of the vessel. The radiation sources are distributed to emit beams of radiation across the interior of the vessel, the wavelength of the radiation being selected such that an interaction such as fluorescence or absorption occurs between the radiation and the chemical species which can be detected by the detectors. A representation of the distribution of the chemical species within the vessel can then be derived from the detected interactions by conventional tomography techniques.

20 Claims, 4 Drawing Sheets

CHEMICAL SPECIES DISTRIBUTION AND MIXTURE MONITORING

BACKGROUND OF THE INVENTION

The present invention relates to apparatus for monitoring the distribution and mixing of chemical species in a region of space such as a vessel or a free space such as a space containing an engine exhaust plume.

The spatial and temporal distribution and mixing of chemical species can be a critical determinant of the performance of chemical reactors. For example, the combustion chamber of an internal combustion engine is a chemical reactor in which the spatial and temporal variation of the air-fuel ratio prior to ignition bas a significant influence on both fuel efficiency and emissions performance. Various attempts have been made to analyse the spatial variation of the air-fuel ratio within internal combustion engines. Typically the cylinders and/or pistons of internal combustion engines have been provided with windows through which it has been possible to take graphs using high-speed camera equipment so as to image variations in the air-fuel ratio. It is known for example to introduce a fluorescent dopant into fuel introduced into the cylinder so as to provide a visual indication of fuel distribution within the air-fuel mixture.

A wide range of tomography modalities have been developed which encompass the classes of hard-field, soft-field and emission techniques. Each of these classes has various strengths and weaknesses. In particular, all of the classes require an inversion calculation to reconstruct the distribution of a parameter of interest. The stimulation process for fluorescence tomography has a hard-field nature in that the only material which can be stimulated to fluoresce is that lying on the geometrical path of input radiation, whilst detection of the isotropically emitted fluorescence clearly has an emission nature.

Work has been conducted in the case of X-ray fluorescence as described by Cesareo R., and Mascarenhas S. (1989), A new tomographic device based on the detection of fluorescent X-rays, Nucl. Instr. Meth. A277, 669–672. This paper points out that collimation of both the stimulation beam and detector acceptance results in an unambiguous determination of the spatial region referred to as the "space-point" from which detected fluorescence photons were emitted. In the described X-ray fluorescence case however the material under study strongly attenuated both the stimulation beam and the fluorescence photons and this required an additional complexity in image reconstruction by de-convoluting the attenuation. Thus this earlier work appeared to indicate that using collimated stimulation beams and detector fields of view did not avoid the need for computationally intensive image reconstruction techniques.

The technique of planar laser-induced fluorescence (PLIF) has been the most successful to date in providing information on the mixing and combustion processes in internal combustion engines. To implement this technique, large glass inserts are placed between the cylinder head and the engine block. The laser emission is formed into a sheet, passing through the cylinder head and exciting fluorescence. The fluorescence is observed in the orthogonal direction through an elongated piston with a central glass window and a mirror, typically by a CCD camera However, PLIF systems can only produce a low number of frames per cycle because of the comparatively low frequency of the light samples, determined by the low repetition rate (10–100 Hz) of the laser sources.

The known systems require extensive optical access which in ton requires substantial modifications to an internal combustion engine the performance of which is to be assessed, The provision of relatively large optical windows in a cylinder wall for example can significantly affect engine performance as compared with an engine in which no such optical windows are provided. Furthermore, the temporal resolution of such known techniques is limited to a few Hertz due to the pulsed laser sources used. These techniques are not suitable for application to routine engine operations.

It is known that air containing hydrocarbons absorbs laser radiation to a greater extent than air fee of hydrocarbons if the laser radiation is at a frequency which excites vibrational/rotational transitions in hydrocarbon molecules. In particular, the presence of $CH_3$, $CH_2$ and CH groups in molecules in an air/hydrocarbon mixture results in a greater absorption due to various vibrational transitions and their overtones and combinations than is the case with air not containing such molecules.

SUMMARY OF THE INVENTION

It is an object of the present invention to exploit the specific absorption of radiation to monitor spatial and temporal variations in the air-fuel ratio within for example an internal combustion engine.

It is a firer object of the present invention to provide an improved apparatus for monitoring the spatial distribution within a vessel of a chemical species without requiring the use of computationally intensive techniques to produce a representation of the distribution.

According to the present invention, there is provided an apparatus for monitoring the distribution within a defined space of a chemical species, wherein a plurality of radiation sources and radiation detectors are distributed around the perimeter of the space, the radiation sources being distributed to emit beams of radiation across the interior of the space, the wavelength of the radiation being selected such that an interaction occurs between the radiation and the chemical species which can be detected by the detectors, and means being provided for deriving a representation of the distribution of the chemical species within the space from the detected interactions.

In one embodiment of the present invention a plurality of radiation sources and radiation detectors are distributed around the perimeter of the space such that radiation from each source is directed along a predetermined path towards at least one detector, the sources emit radiation at a wavelength selected to excite vibrational and/or rotational traditions in at least one of the chemical species such that radiation is absorbed to a greater degree by the said at least one species than by at least one other species, absorption of the radiation occurring along each of the predetermined paths is monitored to provide a measure of the path integral of the concentration of the said at least one species along each path, and a representation of the distribution of the concentration of the said at least one species within the space is derived from the measured path integrals of concentration.

The radiation sources and detectors may be arranged in pairs such that each detector receives radiation via a respective path from a respective source. Alternatively, at least one source may be arranged to direct radiation in a beam defining respective predetermined paths to each of a plurality of detectors, each detector having a collimated field of view which includes only the respective predetermined path.

In the case of the application of the invention to monitoring the spatial variation of air-fuel ratios within internal combustion engines, the specific if weak absorption of electromagnetic radiation in the near infra-red region of the electromagnetic spectrum (1 μm to 2.5 μm) may be exploited to distinguish between absorption resulting from overtones and combinations of various hydrocarbon vibrational and/or rotational transitions, particularly such transitions arising with $CH_3$, $CH_2$ and CH groups in molecules. A suitable wavelength for use in the apparatus of the first embodiment of the present invention is 1700 nm (−15, +50 nm), as hydrocarbons exhibit weak absorption at this wavelength. Thus in contrast to prior art techniques, which rely upon the addition of fluorescent dopants to the fuel, the first aspect of the present invention uses the inherent absorption properties of hydrocarbon systems to derive data described in the spatial variation of the air-fuel ratio without in any way modifying the chemical constituents by for example adding dopants to the fuel. Furthermore, although each source-detector pair can provide a measure of the path integral (or average) of the hydrocarbon concentration only along the path between that pair, the spatial location of that path can be accurately determined and, providing data is extracted from a sufficient number of paths, it is a relatively well known computational task to produce a representation of the distribution of the hydrocarbons using conventional tomographic techniques. The sources may be lasers, and for the engine application the sources should have a high modulation bandwidth, e.g. of the order of 40 kHz or more. Temporal resolutions as high as 20 kHz may thus be achieved, in contrast to the low temporal resolutions achievable with known techniques.

Preferably, each radiation source comprises means for directing radiation having a further wavelength along the predetermined path to the detector of the respective pair, the further wavelength being selected such that it does not excite vibrational and/or rotational transitions in any of the components, and mean are provided for comparing the absorption of the radiation of the two wavelengths to compensate for absorption which is not related to vibrational and/or rotational transitions excited in the said at least one component. A suitable wavelength for the further radiation source is 1550 nm in the case of long-chain saturated hydrocarbons being the species of interest The radiation output of each detector may be time division multiplexed such that only one wavelength is emitted at any one time. Alternatively, frequency division multiplexing may be used, with the absorption of different simultaneously transmitted wavelengths being measured by de-multiplexing by the detector electronics.

In an alternative arrangement, the detectors comprise optical means for distinguishing between optical characteristics of the outputs of the sources which are of different wavelength. The outputs of different wavelength may be differentially polarised, with the optical means being polarisation sensitive, or the optical means may comprise a spectrometer.

Preferably at least one source comprises a tunable laser and means are provided for tuning the laser to take account of variations in the absorption characteristics of the space.

According to a second embodiment of the present invention, each radiation source produces a collimated radiation beam directed along a predetermined respective path to stimulate fluorescence in a chemical species, the detectors being responsive to fluorescence photons emitted by the chemical species, each detector having a collimated field of view which intersects a plurality of the predetermined paths, the apparatus further comprising means for identifying the position of the source of fluorescence photons detected by any detector by correlating the detection of fluorescent photons with the energisation of the sources, and means for deriving a representation of the distribution of the chemical species from the correlated fluorescence photon detection and position data Preferably, means are provided for sequentially energising the sources such that only one beam intersected by the field of view of one detector is energised at a time. An alternative to sequential operation of the sources is to encode each source by intensity modulation at a given frequency, coupled with de-multiplexing of the detector signals.

Each radiation source may comprise a high-power laser, and may deliver a series of pulses of UV wavelength. Alternatively, the sources may be diode lasers, LEDs or may deliver radiation derived from a gas-filled discharge lamp. Each source may produce radiation with a wavelength in the range 200–500 nm The sources may be arranged to generate beams which intersect in regions of the defined space, each intersection region also being intersected by the collimated field of view of at least one detector.

The second embodiment of the present invention makes it possible to determine the concentration of various chemical species in a liquid-phase or gas-phase mixture without requiring a computationally intensive inversion step. Because of the weak attenuation of the stimulation and fluorescence photons, a simple geometrical reconstruction of the true space-points can be used. It is necessary to know the fluorescence properties of the gas or liquid phase subject well in order to ensure that the detected fluorescence photons do indeed come from the target chemical species. It is also necessary to ensure that there can be no ambiguity of the space-point from which fluorescence photons are emitted, either by sequential operation of the sources or by means of encoding each source (for example using frequency encoding).

BRIEF DESCRIPTION OF THE DRAWINGS

Embodiments of the present invention will now be described, by way of example, with reference to the accompanying drawings, in which.

DETAILED DESCRIPTION OF THE INVENTION

Figure 1:
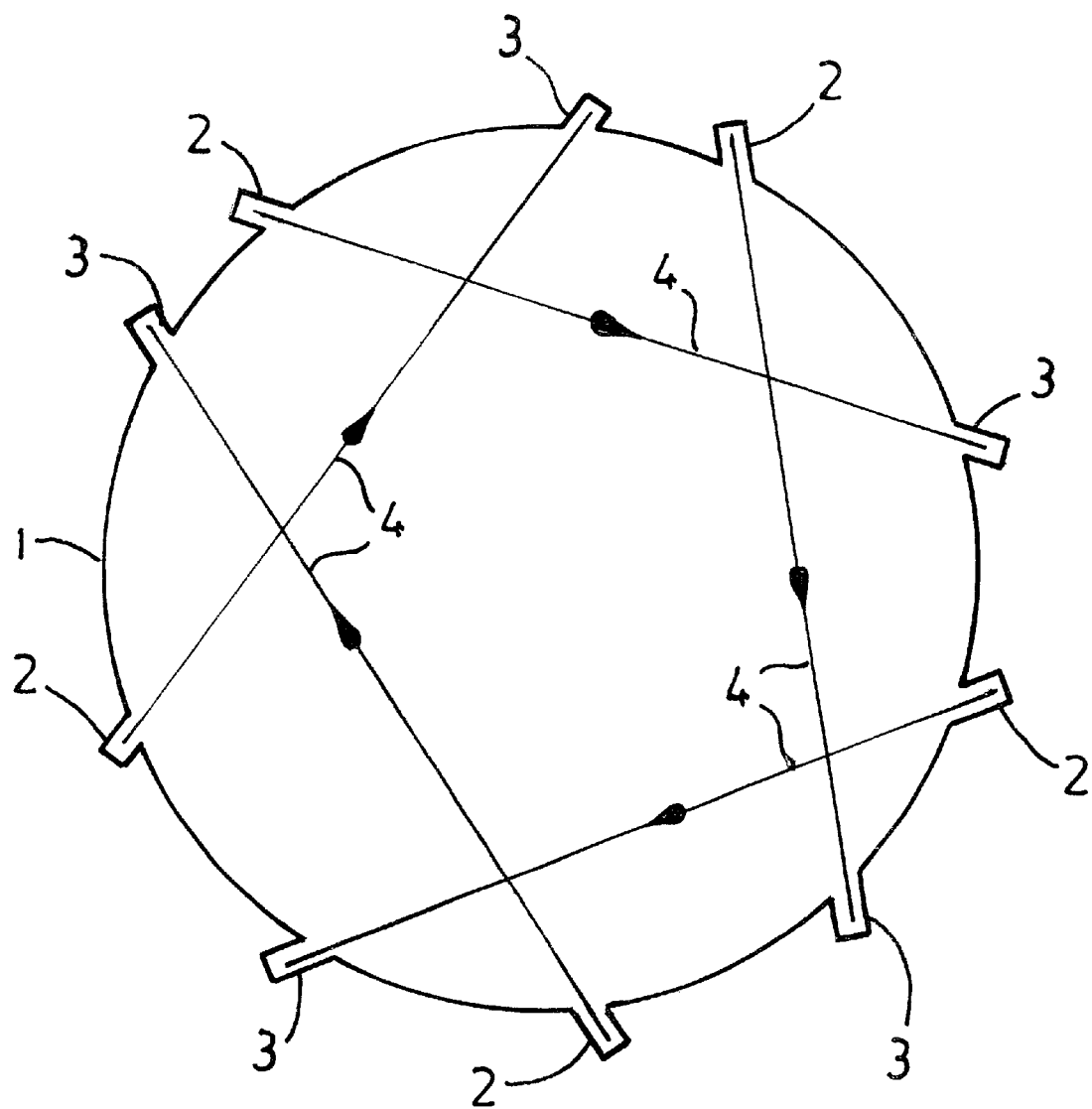
FIG. 1 is a simplified schematic cross sectional view through a vessel showing excitation paths as used in apparatus according to an embodiment of the present invention relying upon beam absorption.

Referring to FIG. 1 of the accompanying drawings, the circle 1 represents the wall of a cylinder of an internal combustion engine, An array of five optical fibre based light sources 2, coupled to a common laser source, is distributed around the periphery of a plane through that cylinder, each source directing a beam towards a respective detector 3, the beams being directed along the paths indicated by lines 4. Each transmitted beam is at a wavelength of 1700 nm±10 nm. Radiation at that wavelength is absorbed due to overtones and combinations of various $CH_3$, $CH_2$ and CH vibrational and/or rotational transitions. In contrast, there is negligible absorption due to other species such as $N_2$, $H_2O$, $CO_2$ etc, which are to be expected in a normal air-fuel mixture. Accordingly the degree of absorption of each of the beams is a function of the concentration of hydrocarbons in the particular beam path In order to improve the signal to noise ratio, account must be taken of non-resonant attenuation, for example by scattering from particles etc. This can be achieved by generating laser radiation at two wavelengths, one of which excites vibrational and/or rotational transitions in hydrocarbons but not in components of air and the other of which does not excite such transitions in either hydrocarbons or air. A comparison of the attenuation of the two radiation beams makes it possible to distinguish between attenuation due to the presence of hydrocarbons and attenuation due to other factors, e.g. particles, temperature variations, or pressure variations. In this embodiment, the non-resonant beam is 1550 nm. Beams of the two wavelengths are launched into the same optical path so that the two beams follow identical paths through the combustion chamber. This is achieved by use of optical fibre couplers designed to operate optimally for these two wavelengths. Such a system has been demonstrated in operation, showing the distribution of a free-flowing hydrocarbon jet issuing from a 5 mm diameter nozzle through a cross-section of a container having 80 mm diameter which is otherwise filled with air.

Monitoring the performance of a cyclical reactor with a rapid cycle time, such as an engine running at say 1800 rpm, can be achieved in a reliable manner by using fast source modulation in order to discriminate against thermal and combustion backgrounds, to define relative intra-cycle minima of absorbence, and to perform time or frequency division wavelength multiplexing. This makes considerable demands on the frequency response of the light sources and detectors. These demands can be met by, for example, using cavity-extended InGaAs laser diode light sources which are available with power outputs of 3 mW coupled into an optic fibre. The available sources have the required stability and a modulation bandwidth which may be about 40 kHz or may be much higher. Thus sources and detectors can be coupled into the cavity defined by the combustion chamber through very small apertures via optic fibres.

Figure 2:
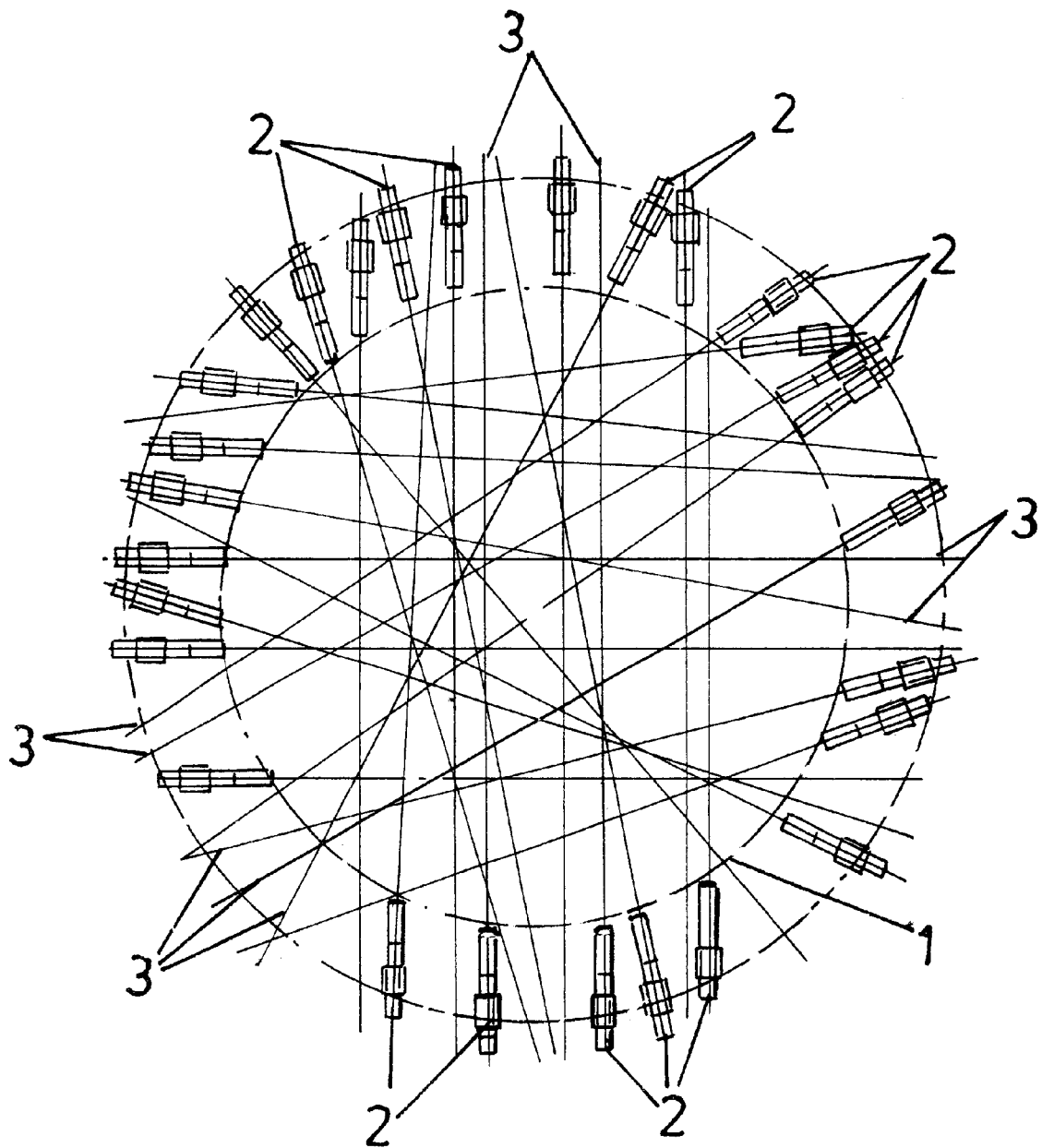
FIG. 2 is a schematic cross sectional view through a vessel showing an arrangement of radiation source and detector pairs in an apparatus of the type shown in FIG. 1 but incorporating twenty eight source/detector pairs.

Since the described system is a "hard-field" mode of tomography, in which the number of reconstructed space points is limited to a number related to the number of absorption paths through the chemical reactor, it is important to have as many absorption paths as possible. This has to be balanced against the power/noise requirements of the system, and the geometrical constraints imposed by the dimensions of the reactor. In the deliberately simplified case illustrated in FIG. 1, only five paths are defined through the chemical reactor. It is anticipated that typically of the order of thirty source-detector pairs will be located in a common plane around an engine cylinder, the number of pairs being larger for larger cylinders. FIG. 2 shows an arrangement having twenty-eight source-detector pairs. Similar arrays of laser sources and detectors could be arranged in a series of axially spaced planes. For example six arrays each of thirty laser source/detector palm could be arranged to provide a total of 180 independent absorption paths through the chemical reactor. By appropriate distribution of these paths sufficient information could be obtained to provide an accurate representation of the air-fuel ratio through an extended portion of the reactor. It will of course be appreciated that in many applications a very much larger number of absorption paths could be readily achieved.

Many options exist to generate spatially distinct optical paths through the subject, which include the use of sources coupled to an optical fibre that is split into multiple fibres as described above. Further options include multiple light sources, a wide fan beam launched into the subject with the detectors being provided with collimated optics such that the output of one source is detected by each of two or more detectors, and the coupling of light from a source simultaneously into several fibres, such as ribbon fibres with each fibre being placed behind a miniature lens.

The radiation sources may include tunable lasers, which may be exploited to de-tune from an absorption peak to a wavelength at which a suitable penetration into the subject could occur. Fine tunability of the radiation sources may be used to ensure optimal balance of penetration versus absorption.

Figure 3:
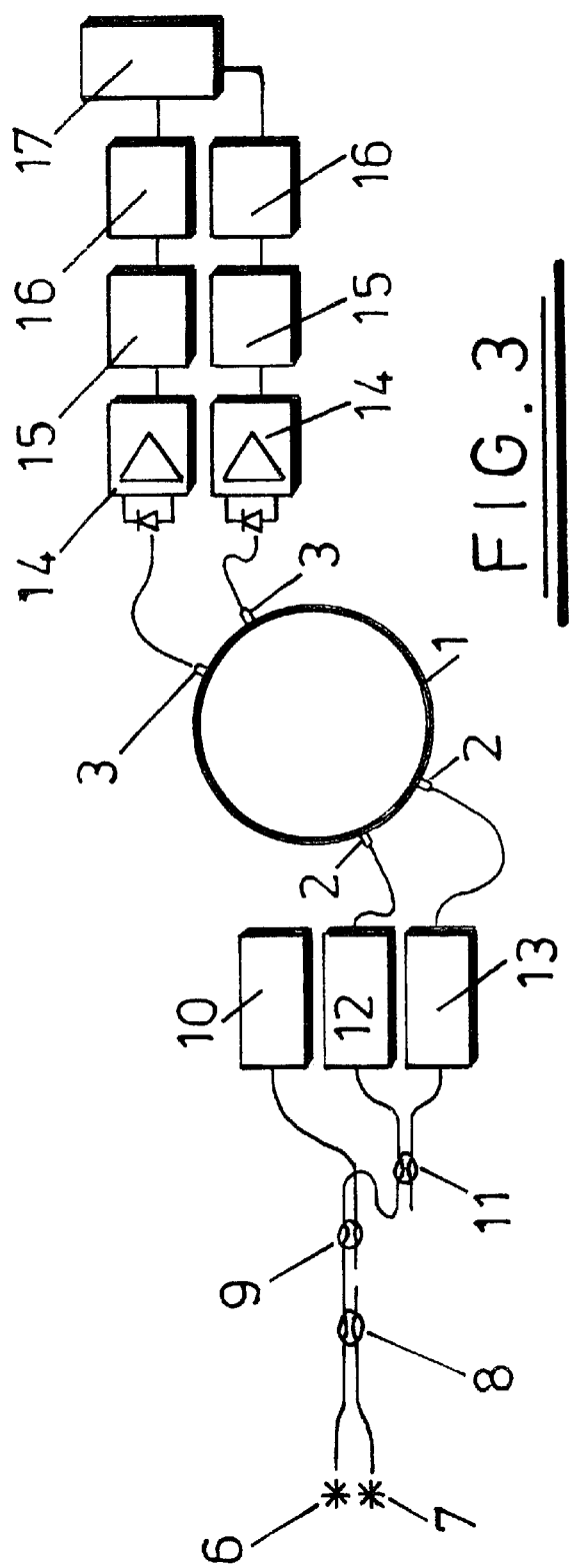
FIG. 3 is a schematic diagram showing components used in apparatus of the type illustrated in FIGS. 1 and 2.

FIG. 3 illustrates a suitable system architecture for the tomographic imaging system described with reference to FIGS. 1 and 2. Laser sources 6 (1550 nm) and 7 (1700 nm) are connected to a WDM coupler 8, one output of which is connected to a 67/33 broadband coupler 9. One output of coupler 9 is connected to a 1×32 coupler 10. The second output of coupler 9 is connected to a 50/50 broadband coupler 11. Each output of coupler 11 is connected to a 1×32 coupler 12, 13. The couplers 12 and 13 are connected to the optical light sources 2 (two only of which are shown) that are arranged around cylinder 1. Detectors 3 are each connected in series to an amplifier 14, a de-multiplexer 15, and an analogue to digital converter 16. A PC 17 is connected to the output of each ADC 16.

Figure 4:
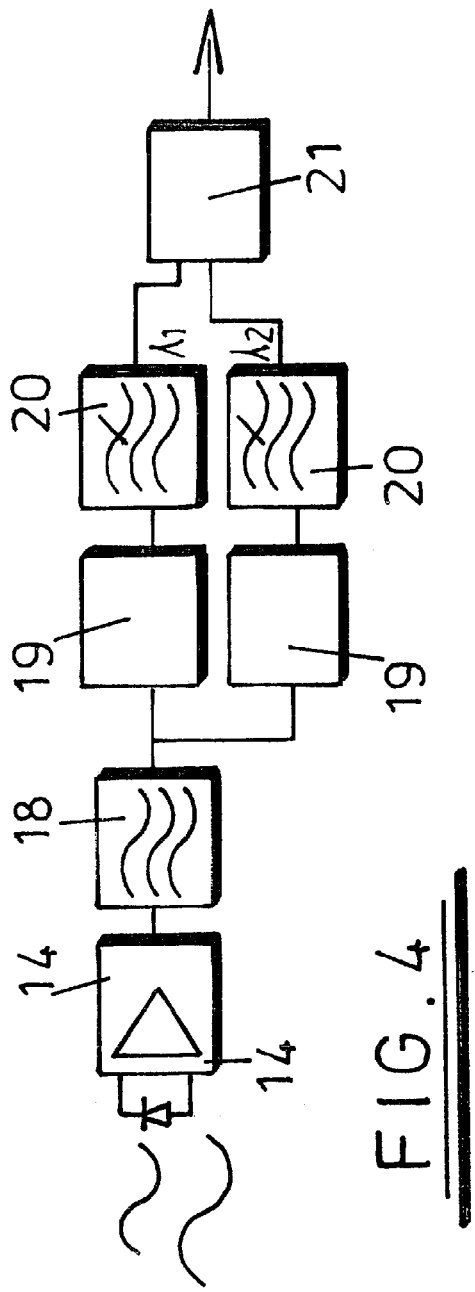
FIG. 4 is a schematic diagram showing the de-multiplexer of FIG. 3 in more detail.

One embodiment of the apparatus uses silica-based optical and integrated-optical couplers. Such devices when used with short fibres are suitable for radiation wavelengths up to 2.2 μm. Separate laser diode (or light emitting diode) sources may be used for each path through the subject, a separate source being used to generate radiation at each wavelength The de-multiplexer 15 is illustrated in more detail in FIG. 4, which shows the front end amplifier 14 connected to a low pass filter 18. A pair of lock-in amplifiers 19 are connected to the low pass filter 18, with each lock-in amplifier being connected to a low pass Bessel filter 20 in order to separate out the two wavelengths. A data acquisition circuit 21 samples the outputs at a sampling rate of >12 kHz in order to feed the results to the ADC 15.

Further components in the system (not shown) may include means to correct for effects due to the pressure of a gas-phase subject, for example, by using radiation having a third wavelength, or by simultaneous pressure measurement. The use of three or more wavelengths in the radiation transmitted through the subject may enable measurement of variations in the local refractive index of the mixture.

The apparatus is not restricted to use in testing of combustion engines, but may be used for any suitable mixture within a prescribed region. For example, the production of esters is typically carried out in glass-lined reactor vessels, so that the radiation sources and detectors may be placed in or around the outer metal hull of the vessel without disrupting the glass lining. In this case, specific absorption by the C=O functional group at about 5.8 microns is a good candidate wavelength for exploitation.

The availability of a tunable diode laser at 3.4 μm in the future may make the use of the fundamental absorption band of long-chain hydrocarbons feasible in the tomographic imaging system described above, instead of the use of the second harmonic of the absorption band as described.

Figure 5:
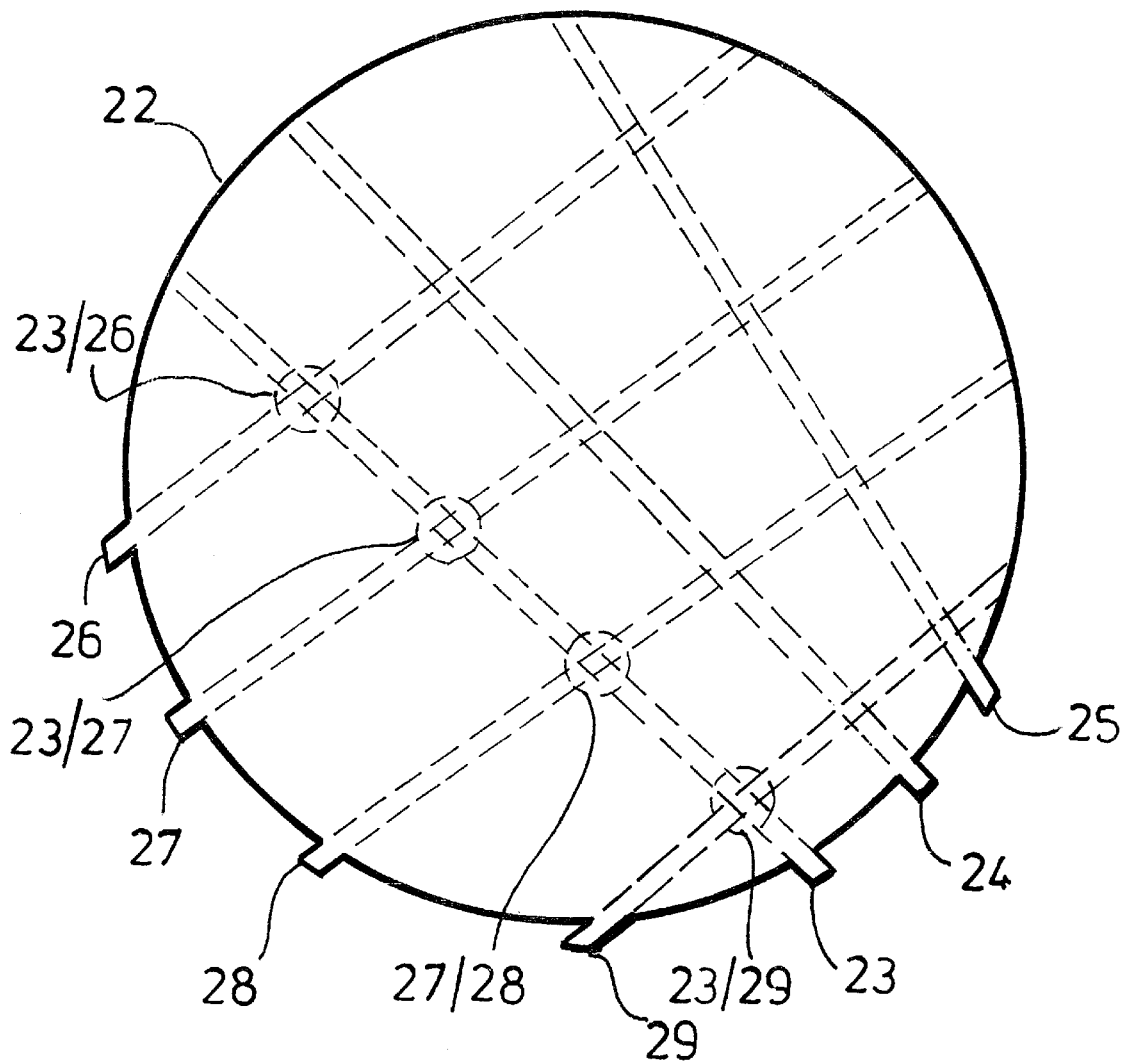
FIG. 5 is a schematic cross sectional view through a vessel showing excitation paths as used in apparatus according to an embodiment of the present invention relying upon fluorescence stimulation.

Referring to FIG. 5 of the attached drawings, the circle 22 indicates the cross-section of a cylinder of an internal combustion engine. Set into the walls of the cylinder are three laser sources 23, 24 and 25 and four detector 26, 27, 28 and 29 which are sensitive to fluorescence photons which will be emitted by a target dopant introduced into the cylinder with a charge of hydrocarbon fuel if the dopant is exposed to radiation from any one of the three sources 23, 24 and 25. The tee sources produce collimated beams as indicated by broken lines and the four detectors have collimated fields of view again indicated by broken lines. The three beams and the four fields of view lie in a common plane such that each of the beams intersects each of the four fields of view. For example, intersections between the beam produced by the source 23 and the fields of view of the four detectors are indicated by dotted circles in the drawing labelled respectively 23126, 23/27, 23/28 and 23/29. Thus the total number of intersections is the product of the number of sources and the number of detectors.

The different sources 23, 24, 25 may be generated as for the first embodiment (eg using optical fibres, multiple light sources, etc), or alternatively, beam deflectors (eg electro-optic or acousto-optic) or switches may be used A further alternative is to have two separate stimulant beams which cross at a point, giving multi-photon stimulation that may be detected by many receivers. This makes it possible to use wavelengths that have a better penetration into the area of interest.

When fuel containing fluorescent dopant is injected into the cylinder, it will mix with air and as a result a non-uniform air/fuel mixture is established within the cylinder. Each of the intersection points between the beams and fields of view defines a space point at which the concentration of the dopant and thus of the associated fuel can be assessed.

If the three sources 23, 24 and 25 produced radiation simultaneously, it would not be possible for any one of the four detectors to distinguish between fluorescence photons emitted by the three beams which intersect the detector's field of view without further modification to the radiation. Accordingly the three sources 23, 24 and 2 are energised sequentially such that at any one time only one beam intersects each of the detectors fields of view. Thus by correlating the energisation of the sources and the outputs of the detectors the intensity of the emitted fluorescence photons at each of the twelve intersection points can be assessed to provide a measure of the localised dopant concentration.

As an alternative to sequential operation of the sources, a means of encoding each radiation source, such as frequency encoding with de-multiplexing on the detector, may be used to detect fluorescence caused by the different radiation sources It will be appreciated that the assembly illustrated in FIG. 5 enables the derivation of data only from a limited planar region of the interior of the cylinder. In practice, a series of arrays of sources and detectors such as that shown in FIG. 5 would be provided in spaced-apart locations along the length of the cylinder so as to enable the fuel/air ratio to be determined at a large number of points within the cylinder. If each coplanar set of sources and detectors incorporates N sources and M detectors, and a total of L sets of sources and detectors are distributed along a length of the cylinder, the total number of space points from which data can be derived is the product of L, N and M.

The fluorescence of several systems has been studied including 3-pentanone in iso-octane (absorbing at 280 nm) and a range of commercial gasolines (absorbing at 320–480 nm). In the former case, 3-pentanone is an artificial dopant which is widely used in fluorescence studies and stimulation sources may be used which are high-power lasers delivering typically 10 ns pulses at 10 Hz. (N.B. The typical performance of pulsed lasers, e.g. 10 Hz, limits known pulsed-laser based imaging techniques to very slow speeds, whereas the present invention permits very high speeds, e.g. 10,000 frames per second or more). (GaN-based blue laser diodes, yielding 5 mW at 410 nm could also be used. The sequential operation combined with the UV wavelength required for fluorescence stimulation of 3-pentanone (285±35 nm) has been found to present difficulties. Further work is being conducted using a set of gas-filled discharge lamps. In the gasoline case, fluorescent species are normally present which yield strong signals upon stimulation over a wide range of wavelengths. In particular, a variety of suitable sources in the range 200–500 nm have been shown to yield suitable signals. Gasoline is stimulated over the range 300–500 nm. Measurable fluorescence signals have been obtained from gas-phase gasoline/air mixtures in a special high temperature high pressure container, using continuous wave UV light sources as the stimulation source at power levels of about 3 mW, and with only one intersection region between the stimulation path and the viewing path of the collimated detection apparatus. There is also the prospect of much more intense opto-electronic sources becoming available based on new solid-state technologies such as GaN and Sb which will ease the problems of sequential operation Accordingly it is believed that sequential operation can be achieved even in arrangements with a large number of space-point beam intersections.

Fluorescence has also been tested in a liquid-phase example, using rhodamine 6G dye added to water. This has demonstrated the operation of the technique, by yielding auto-projected images of the rhodamine dye distribution, with many intersection regions between the sequentially operated stimulation paths and the viewing paths of the collimated detectors.

Fluorescence spectra may be detected as well as the amplitude of the fluorescence by using for example a miniaturised spectrometer. Detection of fluorescence spectra may be used to identify the fluorescence properties of the subject, (eg between different fuel types) and hence to "fingerprint" different species. As gasoline is a mixture of many chemical species, with interdependent emission characteristics, light emission can be expected to vary with the relative concentration of the major aromatic constituents, as well as with the various additive packages, including detergents. Thus, the optical "fingerprint" of the fuel may vary from supplier to supplier, and therefore in time, because of mixing in the vehicle tank. This fingerprinting technique can be exploited to enable reliable air-fuel ratio measurement in any conditions. Hence, reliable combustion control can be attained.

The distribution of fuel in a combustion cylinder in both embodiments of the present invention may be used to predict flame development and to control flame development, thus giving greater engine efficiency.

It will be appreciated that the sources and detectors schematically represented in the drawings could be coupled to a combustion cylinder via optical fibres such that a large number of signals could be coupled to and from the cylinder through optical fibres extending through small holes formed in the cylinder wall. The provision of such small holes would not substantially affect the conditions within the combustion cylinder as compared with an equivalent engine not provided with monitoring optical fibres. Accordingly problems associated with prior art devices requiring large area "windows" are avoided. Minimal optical access is required to the vessel, either all in one plane for 2-D measurements, in several stacked planes for 3-D measurements, or for the generation of true 3-D images by non-planar sets of pats through the subject It will also be appreciated that the techniques of the present invention can be applied to measure any subject which presents low attenuation to the stimulant and fluorescence photons, and particularly in many low-absorption hydrocarbon systems, for example turbine engines.

It will be appreciated that for both described embodiments of the present invention there are no mechanical moving parts employed either to provide multiple beam paths through the reactor or cylinder, or to change the wavelength of light. The system is therefore all opto-electronic.

What is claimed is:

1. An apparatus for monitoring the distribution within a defined space of a chemical species, wherein a plurality of radiation sources and radiation detectors are distributed around the perimeter of the space such that beams of radiation are emitted across the space and radiation from each source is directed along a predetermined path towards at least one detector, the sources emit radiation at a wavelength selected to excite vibrational and/or rotational transitions in at least one of the chemical species such that radiation is absorbed to a greater degree by the said at least one species than by at least one other species, absorption of the radiation occurring along each of the predetermined paths is monitored to provide a measure of the path integral of the concentration of the said at least one species along each path, and a representation of the distribution of the concentration of the said at least one species within the space is derived from the measured path integrals of concentration.

2. An apparatus according to claim 1, wherein the radiation sources and detectors are arranged in pairs such that each detector receives radiation via a respective path from a respective source.

3. An apparatus according to claim 1, wherein at least one source directs radiation in a beam defining respective predetermined paths to each of a plurality of detectors, each detector having a collimated field of view which includes only the respective predetermined path.

4. An apparatus according to claim 1, wherein the species include hydrocarbons and air, and the selected wavelength is 1700 nm.

5. An apparatus according to claim 1, wherein each radiation source comprises means for directing radiation having a further wavelength along the predetermined path to the detector of the respective pair, the further wavelength being selected such that it does not excite vibrational and/or rotational transitions in any of the components, and means being provided for comparing the absorption of the radiation of the two wavelengths to compensate for absorption which is not related to vibrational and/or rotational transitions excited in the said at least one component.

6. An apparatus according to claim 5, wherein the further radiation has a wavelength of 1550 nm.

7. An apparatus according to claim 5, wherein the radiation output of each source is time division multiplexed such that only one wavelength is emitted at a time.

8. An apparatus according to claim 5, wherein the radiation output at each wavelength is intensity modulated at frequencies such that both wavelengths are emitted simultaneously, and wherein the detection system comprises electronic frequency de-multiplexing circuits to distinguish the detected signals due to each of the two wavelengths.

9. An apparatus according to claim 5, wherein the detectors comprise optical means for distinguishing between optical characteristics of the outputs of the sources which are of different wavelength.

10. An apparatus according to claim 9, wherein the outputs of different wavelength are differentially polarised, and the optical means are polarisation sensitive.

11. An apparatus according to claim 9, wherein the optical means comprises a spectrometer.

12. An apparatus according to claim 1, wherein at least one source comprises a tunable laser and means are provided for tuning the laser to take account of variations in the absorption characteristics of the space.

13. An apparatus for monitoring the distribution within a defined space of a chemical species, wherein a plurality of radiation sources and radiation detectors are distributed around the perimeter of the space, the radiation sources being distributed to emit beams of radiation across the space, the wavelength of the radiation being selected such that an interaction occurs between the radiation and the chemical species which can be detected by the detectors, means are provided for deriving a representation of the spatial distribution of the chemical species within the space from the detected interactions, each radiation source produces a collimated radiation beam directed along a predetermined respective path to stimulate fluorescence in a chemical species, the detectors are responsive to fluorescence photons emitted by the chemical species, each detector has a collimated field of view which intersects a plurality of the predetermined paths, and the apparatus further comprises means for identifying the position of the source of fluorescence photons detected by any detector by correlating the detection of fluorescent photons with the energisation of the sources, and means for deriving a representation of the distribution of the chemical species from the correlated fluorescence photon detection and position data.

14. An apparatus according to claim 13, comprising means for sequentially energising the sources such that only one beam intersected by the field of view of one detector is energised at a time.

15. An apparatus according to claim 13, wherein each source is intensity modulated at a specific frequency, and means are provided to de-multiplex the detector signals.

16. An apparatus according to claim 13, wherein each source is a high-power laser.

17. An apparatus according to claim 16, wherein each laser source delivers a series of pulses of UV wavelength.

18. An apparatus according to claim 13, wherein each source delivers radiation derived from a gas-filled discharge lamp.

19. An apparatus according to any of claims 13 to 18, wherein each source produces radiation with a wavelength in the rage 200–500 nm.

20. An apparatus according to any one of claims 13 to 19 wherein the sources are arranged to generate beams which intersect in regions of the defined space, and each intersection region is also intersected by the collimated field of view of at least one detector.

* * * * *